US009271853B2

(12) United States Patent
Skousen et al.

(10) Patent No.: US 9,271,853 B2
(45) Date of Patent: Mar. 1, 2016

(54) VASCULAR STENTS AND RELATED METHODS

(71) Applicant: Brigham Young University, Provo, UT (US)

(72) Inventors: Darrell J. Skousen, Lehi, UT (US); Brian D. Jensen, Orem, UT (US); Anton E. Bowden, Lindon, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 14/533,979

(22) Filed: Nov. 5, 2014

(65) Prior Publication Data
US 2015/0164664 A1    Jun. 18, 2015

Related U.S. Application Data

(63) Continuation-in-part of application No. 14/043,787, filed on Oct. 1, 2013.

(60) Provisional application No. 61/900,211, filed on Nov. 5, 2013, provisional application No. 61/708,616, filed on Oct. 1, 2012.

(51) Int. Cl.
*A61F 2/915* (2013.01)
*A61F 2/86* (2013.01)

(52) U.S. Cl.
CPC . *A61F 2/86* (2013.01); *A61F 2/915* (2013.01); *A61F 2002/91558* (2013.01); *A61F 2250/0036* (2013.01)

(58) Field of Classification Search
CPC ..................... A61F 2/915; A61F 2250/0036
See application file for complete search history.

(56) References Cited

U.S. PATENT DOCUMENTS

| 6,231,598 | B1 | 5/2001 | Berry et al. | |
| 6,241,762 | B1 | 6/2001 | Shanley | |
| 6,699,278 | B2 * | 3/2004 | Fischell et al. | 623/1.15 |
| 8,292,945 | B2 | 10/2012 | Welsh et al. | |
| 2001/0044652 | A1 | 11/2001 | Moore | |
| 2003/0055487 | A1 * | 3/2003 | Calisse | 623/1.15 |
| 2006/0030930 | A1 * | 2/2006 | Burgermeister et al. | 623/1.15 |
| 2006/0271170 | A1 | 11/2006 | Gale et al. | |
| 2007/0191926 | A1 * | 8/2007 | Nikanorov et al. | 623/1.15 |
| 2009/0163989 | A1 | 6/2009 | Contiliano et al. | |
| 2010/0104849 | A1 * | 4/2010 | Lashmore et al. | 623/1.15 |
| 2010/0244329 | A1 | 9/2010 | Hossainy et al. | |
| 2012/0041543 | A1 | 2/2012 | Huang et al. | |

* cited by examiner

*Primary Examiner* — David Isabella
*Assistant Examiner* — Suba Ganesan
(74) *Attorney, Agent, or Firm* — Thorpe North & Western, LLP

(57) ABSTRACT

A vascular stent assembly includes at least a first and a second strut, each including a thickness and a depth. The assembly includes a pair of end radii, with each of the first and second struts extending from one of the pair of end radii. A thickness of at least one of the first and second struts includes a tapering profile extending from one of the end radii to another of the end radii, the tapering profile following a continuously increasing or decreasing function through at least half a length of the at least one strut.

17 Claims, 5 Drawing Sheets

VASCULAR STENTS AND RELATED METHODS

PRIORITY

Priority is claimed of U.S. Provisional Patent Application Ser. No. 61/900,211, filed Nov. 5, 2013, which is hereby incorporated herein by reference in its entirety. This application is also a continuation-in-part of U.S. patent application Ser. No. 14/043,787, filed Oct. 1, 2013, which claims the benefit of U.S. Provisional Application No. 61/708,616, filed Oct. 1, 2012.

BACKGROUND

The leading cause of death in the United States is heart disease, claiming approximately 24% of all deaths. Coronary artery disease is a condition where coronary arteries narrow due to fatty plaque build up, reducing the blood flow to the heart which can lead to heart failure and death. A minimally invasive procedure called percutaneous coronary intervention (PCI) including balloon and stent angioplasty has been developed to treat coronary artery disease.

There are two major complications associated with PCI: restenosis (renarrowing) and thrombosis (blood clots). Restenosis is caused by a combination of early elastic recoil, negative remodeling, and neointimal formation. Early elastic recoil occurs immediately, and is due to the elastic properties of the arteries. Late lumen loss in balloon angioplasty is caused by neointima formation (tissue in-growth) and negative remodeling (arterial shrinking). In stent angioplasty, a cylindrical scaffold wire mesh (stent) typically made of stainless steel is implanted in the artery to prevent restenosis. These stents prevent elastic recoil and negative remodeling, however, neointimal formation can still lead to restenosis.

Stents have proven to reduce the rates of restenosis more than angioplasty alone. Drug-eluting stents have further reduced restenosis rates, but there is a concern for their ability to prevent late-term thrombosis. New stent materials that can improve these two complications associated with existing coronary stents will be advantageous in stent development.

SUMMARY OF THE INVENTION

In accordance with one embodiment, the invention provides a vascular stent assembly, including at least a first and a second strut, each including a thickness and a depth. A pair of end radii can also be provided, with each of the first and second struts extending from one of the pair of end radii. A thickness of at least one of the first and second struts can include a tapering profile extending from one of the end radii to another of the end radii. The tapering profile can follow a continuously increasing or decreasing function through at least half a length of the at least one strut.

In accordance with another aspect of the invention, a vascular stent assembly is provided, including a series of struts, each including a length, a thickness and a depth. A series of end radii can also be provided, each of the struts extending between one end radii on one end of the strut and another end radii on another end of the strut. A thickness of each of the struts includes a tapering profile extending from one end of the strut to another end of the strut, the thickness of the tapering profile continuously increasing or decreasing along the length of the strut through at least half a length of the strut. The depth of each of the struts can be substantially constant along the length of the strut.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Figure 1:
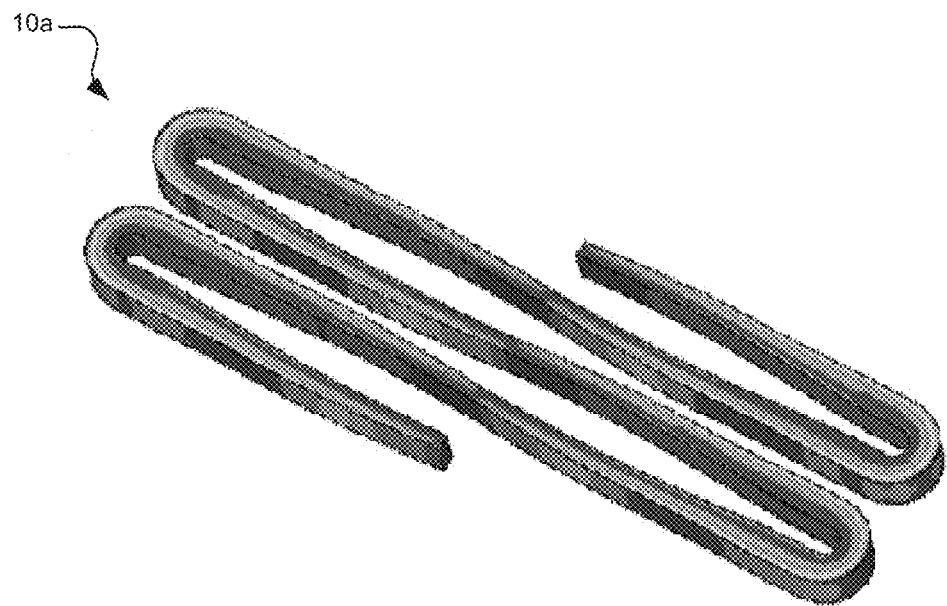
FIG. 1 is a perspective view of selected segments of a stent in accordance with an embodiment of the invention.

Reference will now be made to the exemplary embodiments illustrated, and specific language will be used herein to describe the same. It will nevertheless be understood that no limitation of the scope of the invention is thereby intended.

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention.

In describing and claiming the present invention, the following terminology will be used.

As used herein, relative terms, such as "upper," "lower," "upwardly," "downwardly," "vertically," etc., are used to refer to various components, and orientations of components, of the systems discussed herein, and related structures with which the present systems can be utilized, as those terms would be readily understood by one of ordinary skill in the relevant art. It is to be understood that such terms are not intended to limit the present invention but are used to aid in describing the components of the present systems, and related structures generally, in the most straightforward manner.

As used herein, the term "substantially" refers to the complete or nearly complete extent or degree of an action, characteristic, property, state, structure, item, or result. As an arbitrary example, when an object or group of objects is/are referred to as being "substantially" symmetrical, it is to be understood that the object or objects are either completely symmetrical or are nearly completely symmetrical. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. As an arbitrary example, an opening that is "substantially free of" material would either completely lack material, or so nearly completely lack material that the effect would be the same as if it completely lacked material. In other words, an opening that is "substantially free of" material may still actually contain some such material as long as there is no measurable effect as a result thereof.

As used herein, the term "about" is used to provide flexibility to a numerical range endpoint by providing that a given value may be "a little above" or "a little below" the endpoint.

Directional terms, such as "upper," "lower," "inward," "distal," "proximal," etc., are used herein to more accurately describe the various features of the invention.

Unless otherwise indicated, such terms are not used to in any way limit the invention, but to provide a disclosure that one of ordinary skill in the art would readily understand. Thus, while a component may be referenced as a "lower" component, that component may actually be above other components when the device or system is installed within a patient. The "lower" terminology may be used to simplify the discussion of various figures.

Distances, forces, weights, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a numerical range of "about 1 inch to about 5 inches" should be interpreted to include not only the explicitly recited values of about 1 inch to about 5 inches, but also include individual values and sub-ranges within the indicated range. Thus, included in this numerical range are individual values such as 2, 3, and 4 and sub-ranges such as from 1-3, from 2-4, and from 3-5, etc.

This same principle applies to ranges reciting only one numerical value and should apply regardless of the breadth of the range or the characteristics being described.

Invention

Many of the issues affecting existing vascular stents (including restenosis, thrombosis, and the need for anticoagulant drug therapy (blood thinners)) can be improved or eliminated by using a more biocompatible material. However, significant challenges have existed for the design of stents from ceramic materials. As stents are compliant, expanding and contracting mechanisms, it can be difficult to design effective stents from somewhat brittle materials.

The present technology addresses these limitations by providing a biocompatible coronary stent that can be formed from a variety of materials, even relatively brittle materials heretofore thought unsuitable for such applications. While the invention is not limited to such a material, the present inventors have found that stents formed from carbon-infiltrated carbon nanotubes (or "CI-CNTs") can be used very effectively with existing treatment regimes. In addition to CI-CNTs, other materials can also be used, including, without limitation, shape memory alloys, nitinol, stainless steel, polymers, bioabsorbable polymers, and the like.

Nearly all existing coronary stents have the same basic features, including thin struts that are connected in a zigzag pattern. The strut connection (referred to below as the end radius) is rounded to reduce the stress concentration. The struts and connection form a basic stent segment that is repeated circumferentially around the stent.

Vascular stents undergo a large amount of deflection during insertion. Due to the relatively high strain and elastic properties of CI-CNTs, the present stents can be formed from this material and can be fabricated in their "expanded" state and be elastically compressed for insertion into the body. The present technology optimizes many compliant geometries for compression to create usable stent mesh patterns.

In one particular example, a form of pyrolytic carbon ("PyC") has been developed by the present applicant that allows high manufacturing tolerances (1-3 micron) and also has excellent mechanical properties. The CI-CNT stents of the present technology can be formed from this type of PyC. The PyC can be manufactured by growing a forest of carbon-nanotubes and then infiltrating the carbon nanotubes with carbon graphite. Using MEMS manufacturing processes, a mask can be made with a detailed 2-dimensional geometry. Carbon-nanotubes are grown vertically extruding the 2-dimensional geometry into a 3-dimensional carbon-nanotube forest. The forest is then infiltrated with carbon graphite by a vapor deposition method. The mechanical properties as well as the mass is dominated by the filler material. The biocompatible properties of these CI-CNTs can be expected to be similar to other common methods of manufacturing PyC.

The current stent designs are optimized to provide the maximum possible radial force without exceeding the allowable stress. By reducing the stent strut thickness, as discussed in more detail below, the stresses can be lowered as needed. However, a trade-off occurs as radial stiffness/force decreases with decreased thickness. The stresses and reaction forces for the basic stent segment can be calculated using mechanics of materials equations as well as the pseudo-rigid-body model for compliant mechanisms.

The basic stent segment can be optimized using an exhaustive search with discrete values for continuous variables. These constraints allow a tensile stress less than 80 MPa, a compressive stress less than 120 MPa, and no physical contact (clash) between the stent segments. The optimal design can have the largest possible thickness without exceeding the allowable stress. Also, the optimal strut angle can be the smallest possible angle that can be achieved without the segments clashing before reaching a ⅔ (67%) compression state is reached. A smaller radius can perform better, but may be limited by high compressive stresses on the inner edge of the partial ring.

A tapered beam can be used in the present implementation instead of a constant thickness beam. The struts can be modified from the traditional straight design to a slightly curved design, in order to avoid clashing. In one exemplary embodiment, the stent is designed to have a radial depth of about 100 μm with 12 circumferentially repeating segments.

The improved design results in stresses that are much more uniformly distributed, and adjacent stent segments that do not clash together. The present improvements tripled the reaction force compared to conventional designs while only slightly increasing the maximum tensile stress. While the invention is not so limited, in one embodiment the strut includes a length of about 1 mm and a thickness of about 0.025 mm.

The performance of the stent design can be analyzed using an FE arterial model. The stent can be compressed to its crimped (compressed) condition and then moved into the artery and allowed to spring back pushing against the artery wall. In one test, the artery was pressurized at 100 mmHg, and had an initial minimum lumen diameter of 2.00 mm. After the stent was released, the artery expanded to have a minimum lumen diameter of 2.05 mm.

FEA of the stent design shows that the stresses were much more uniformly distributed across the stent surface (see FIG. 1, for example). Adjacent strut segments did not clash together. Although the struts can be initially curved, when they are compressed they become nearly flat. In this test, the maximum tensile stress was about 82.1 MPa, with a max compressive stress of 165 MPa. The reaction force was 9.1 mN. Even after accounting for a change in radial depth and the overall length of the stent segments, the current stent design showed more than a three-fold increase in the reaction force over conventional designs while only slightly increasing the maximum tensile stress.

Turning now to the figures, FIG. 1 illustrates an exemplary stent segment or assembly 10a in accordance with an embodiment of the invention. FEA analysis of this design reveals that the tensile stresses (1$^{st}$ principal) are distributed much more uniformly than with conventional designs. The struts of this design (discussed in more detail below) do not clash together even under a 65% compression.

Figure 7:
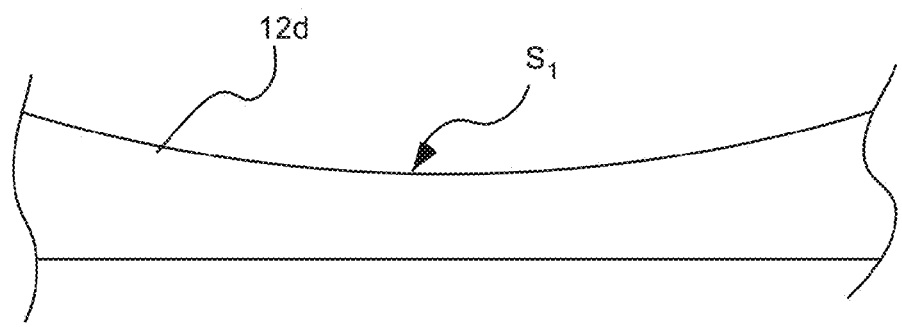
FIG. 7 is a side, partial view of another stent strut in accordance with an embodiment of the invention.
Figure 8:
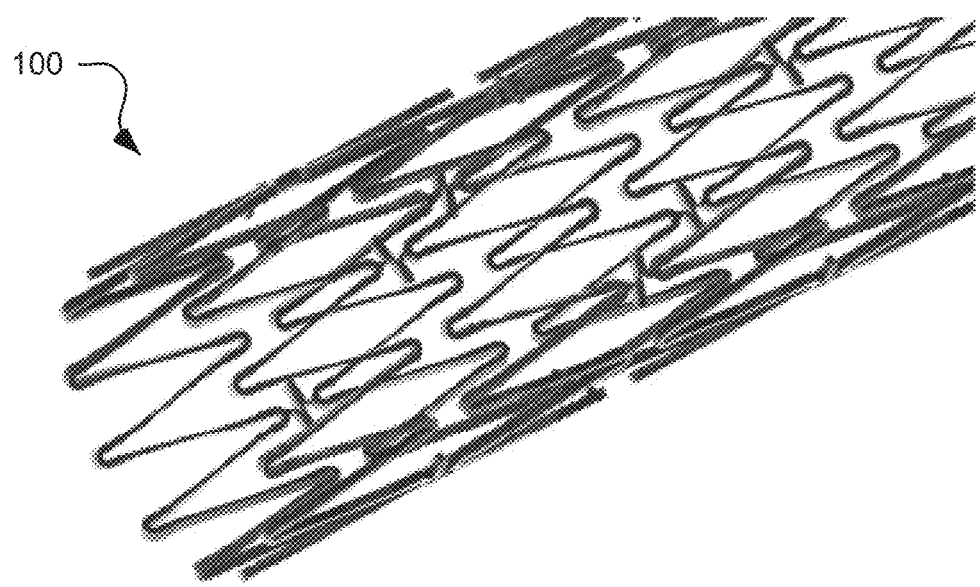
FIG. 8 is a perspective, partial view of a cylindrical stent assembly in accordance with an embodiment of the invention.
Figure 9:
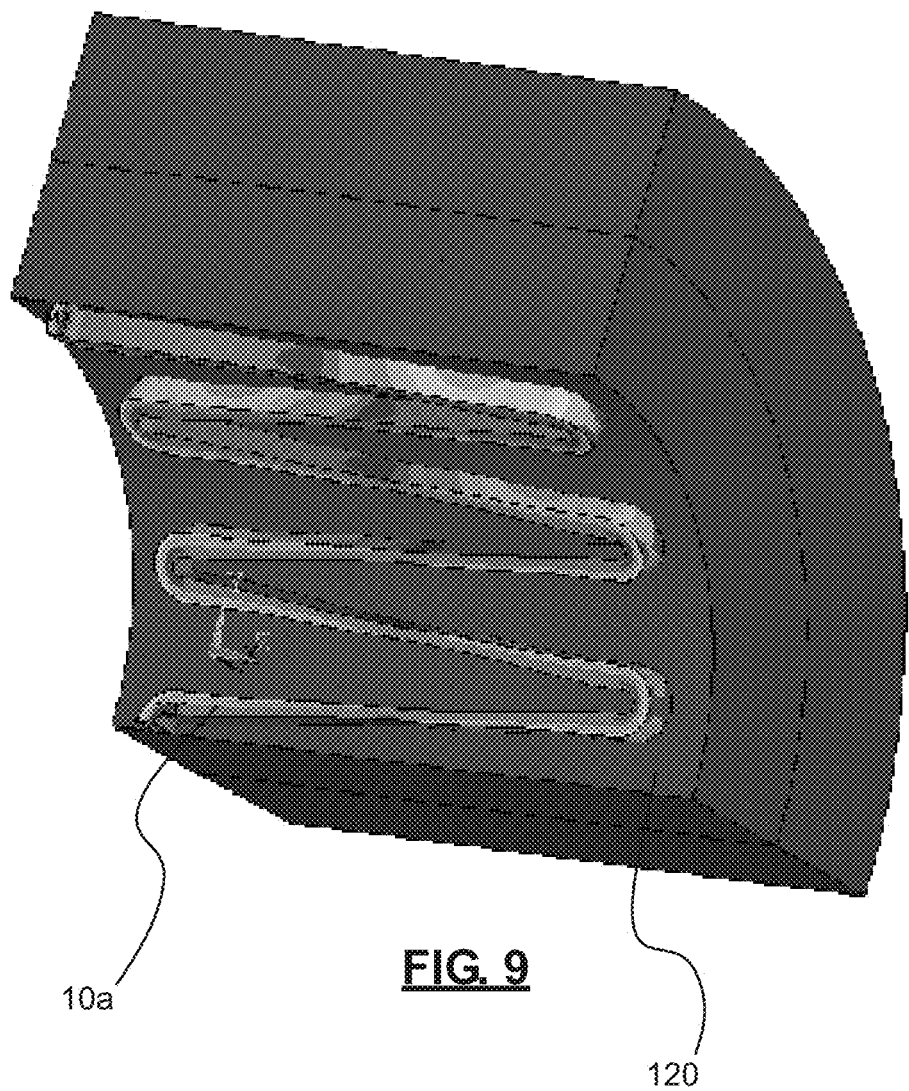
FIG. 9 is a perspective, partially sectioned view of a stent assembly installed within an artery in accordance with an embodiment of the invention.

While only a few segments of the stent technology is shown in FIGS. 1-7 and 9, one of ordinary skill in the art will readily appreciate that the completed stent assembly 100 will appear similar to the example shown in FIG. 8. Thus, each of the various struts, end radii, connecting members, etc., are generally formed into a contiguous mesh pattern (generally cylindrical in shape), to allow the stent to perform within an artery or other body.

Figure 2:
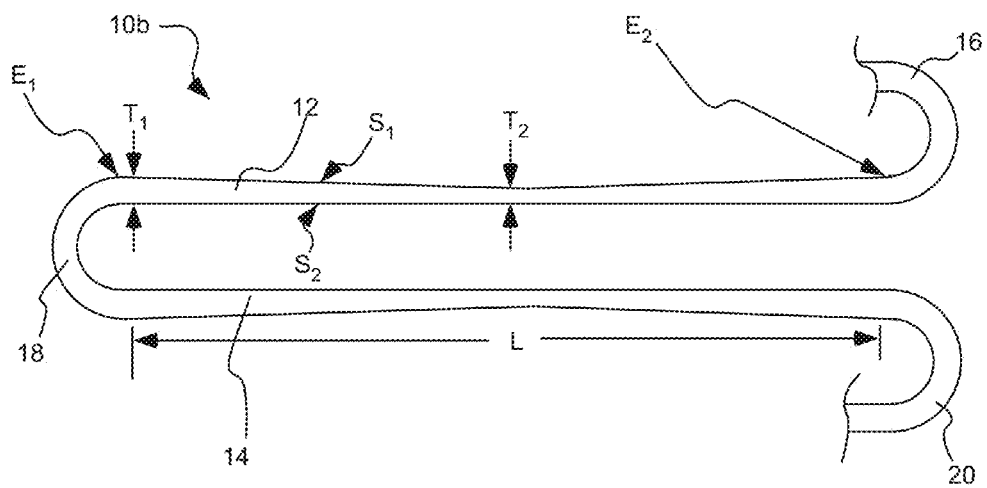
FIG. 2 is a side view of two struts and three end radii of a stent segment in accordance with an embodiment of the invention.

FIG. 2 illustrates in more detail the various components of the overall stent assembly. As shown here, the stent assembly 10b includes a first 12 and a second 14 strut. Each of the struts includes a thickness, shown in the figures as the dimension running from the top to the bottom of the page (see, e.g., thicknesses $T_1$ and $T_2$). The struts also include a depth, which is the dimension running into the page of FIG. 2. The struts include a length, indicated by example at "L" in FIG. 2. Each of the struts extends from, or is coupled to, or joins with one or more end radii 16, 18, 20, etc.

A thickness of at least one of the struts 12, 14 in each strut pair can include a tapering profile that extends from one of the end radii (E1, for example) to another of the end radii (E2, for example). The tapering profile can follow a substantially continuously increasing or decreasing function through at least half a length of the strut. In other words, the tapering profile varies along the length of the strut, but does not generally include any sections where the slope of the taper changes direction. One exception to this condition can occur at the midpoint of the strut (near the thickness indicated at $T_2$ in FIG. 2), where the tapering function can change. Thus, in the example shown in FIG. 2, the thickness of strut 12 is at a maximum near end radius 18 (shown by $T_1$). The thickness of the strut 12 continuously tapers (decreases) along the length of the strut, until it reaches the midpoint of the strut. As such, thickness $T_2$ is smaller than thickness $T_1$. In this particular example, the thickness taper changes at the midpoint of the beam and begins to increase along the length toward end radius 16.

This tapering design can provide stent segments in which stresses are much more uniformly distributed across the stent surface (as illustrated in FIG. 1, for example). In addition, adjacent stent segments (e.g., struts 12 and 14) are much less likely to "clash" or contact one another when in a compressed condition.

The tapering can follow nearly any substantially continuously increasing or decreasing function along the length of the strut. The example shown in FIG. 1 includes a curvilinear tapering that occurs on both faces of the strut. The example shown in FIG. 2 includes a linear slope on each end of the strut that converges at a midpoint of the strut. While the slopes in this example converge at a midpoint, in some embodiments, the slopes can converge at differing points along the length of the strut (or not converge at all, in those cases where only a single taper is provided).

Thus, the taper shown in FIG. 2 includes the case where the upper face or side $S_1$ of strut 12 exhibits a slope, but the lower face or side $S_2$ does not slope. In the example shown in FIG. 4, side $S_1$ of strut 12a includes a substantially constant, linear slope along substantially the entire length of the strut. In the example shown in FIG. 5, strut 12b includes a single side or face $S_1$ that slopes in a curved function. As shown by strut 12c in FIG. 6, one face or side $S_1$ can be convex, in addition to the concave examples provided elsewhere. FIG. 7 illustrates a concave taper in face $S_1$ of strut 12d that is continuously curved across the length of the strut, with a transition occurring at the midpoint of the strut.

In addition to the tapering profiles explicitly shown in the figures, the depth of the struts can also vary along the length of the struts. In other words, the strut can narrow (or broaden) in either or both a direction of thickness or depth, as any particular design my dictate.

Figure 3:
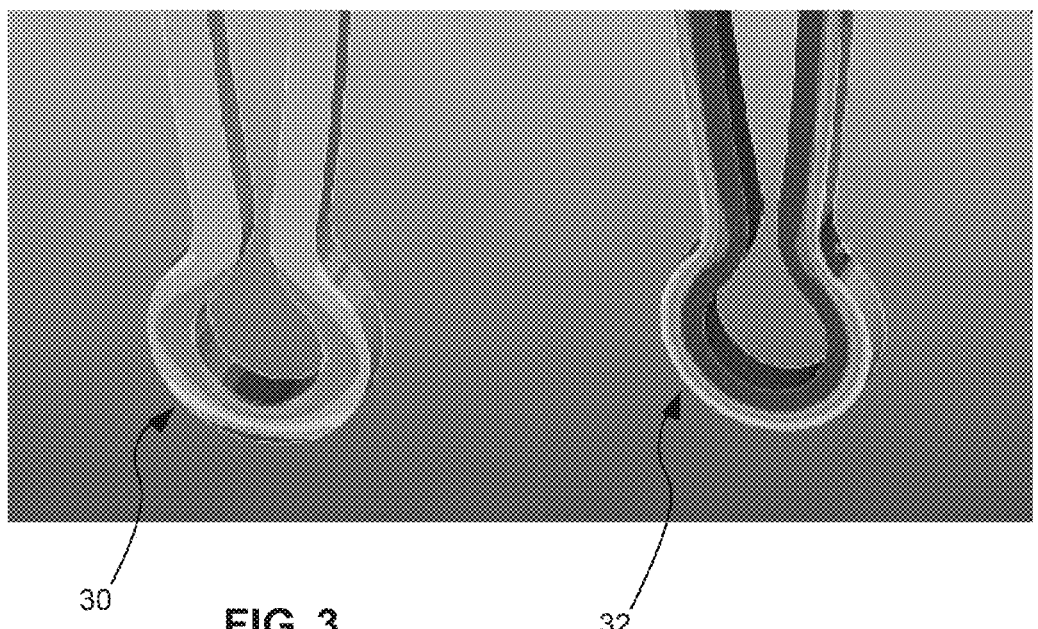
FIG. 3 is a perspective view of end radii of a conventional stent and a stent in accordance with the present technology.
Figure 4:
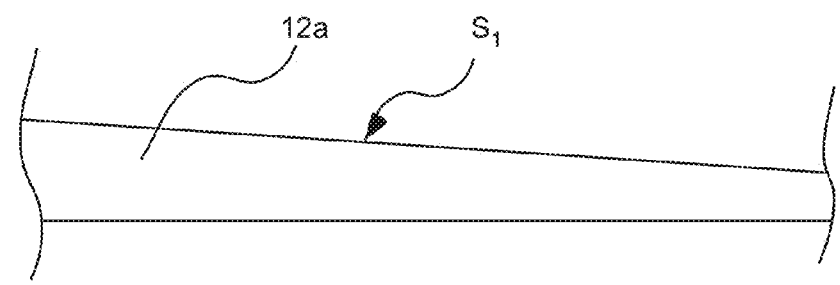
FIG. 4 is a side, partial view of a stent strut in accordance with an embodiment of the invention.
Figure 5:
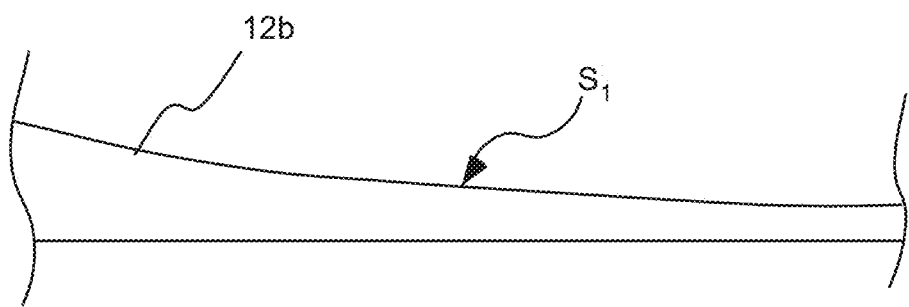
FIG. 5 is a side, partial view of another stent strut in accordance with an embodiment of the invention.
Figure 6:
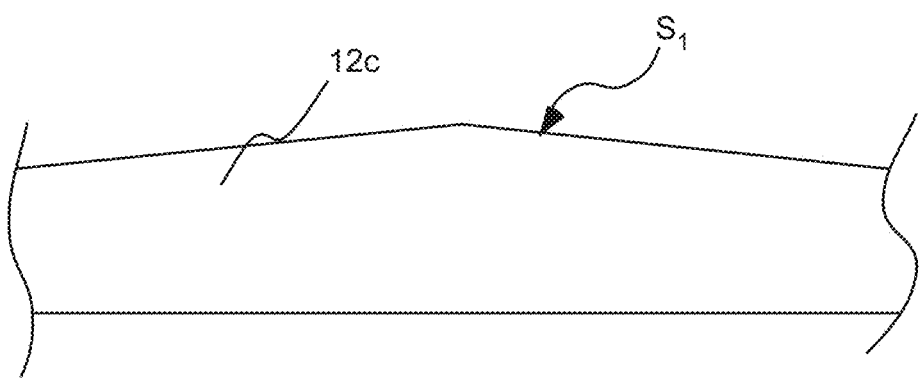
FIG. 6 is a side, partial view of another stent strut in accordance with an embodiment of the invention.

The end radii 16, 18, 20, etc. can vary in both size and design. In the examples shown in FIGS. 1 and 2, the end radii are relatively simple curvatures that gradually transition from one strut to another. As shown in FIG. 3, however, the end radii can include an oversized stress relief pattern that can aid in avoiding stress concentrations in these areas. The end radius 30 shown on the left of FIG. 3 is from a conventional stent design, while the end radius 32 shown on the right of FIG. 3 is from the present design. As the FEA patterns illustrate in these examples, the present design is much more effective at evenly distributing stress along the entire stent assembly, as opposed to the conventional design, which includes high stress concentration at the end radii.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by any claims associated with this or related applications.

We claim:

1. A vascular stent assembly, comprising:
   at least a first and a second strut, each including a thickness and a depth; and
   a pair of end radii, each of the first and second struts extending from one of the pair of end radii; wherein
   a thickness of at least one of the first and second struts includes a tapering profile extending from one of the end radii to another of the end radii, the tapering profile following a continuously increasing or decreasing function through at least half a length of the at least one strut, and wherein the assembly is formed from graphite carbon-infiltrated carbon nanotubes (CI-CNTs).

2. The assembly of claim 1, wherein the tapering profile continuously decreases from one of the end radii to a midpoint of the strut, then continuously increasing from the midpoint of the strut to the other of the end radii.

3. The assembly of claim 1, wherein the tapering profile is a curvilinear profile.

4. The assembly of claim 1, wherein the tapering profile is a sloped line.

5. The assembly of claim 1, wherein the tapering profile is convex.

6. The assembly of claim 1, wherein the tapering profile is concave.

7. The assembly of claim 1, wherein one face of the strut is substantially unsloped, and wherein an opposing face of the strut includes the tapering profile.

8. The assembly of claim 1, wherein opposing faces of the strut each include a tapering profile.

9. The assembly of claim 1, wherein a depth of at least one of the struts can vary along a length of the strut as the thickness of the strut varies.

10. A vascular stent assembly, comprising:
  - a series of struts, each including a length, a thickness and a depth; and
  - a series of end radii, each of the struts extending between one end radius on one end of the strut and another end radius on another end of the strut; wherein
  - a thickness of each of the struts includes a tapering profile extending from one end of the strut to another end of the strut, the thickness of the tapering profile continuously increasing or decreasing along the length of the strut through at least half a length of the strut; and
  - the depth of each of the struts being substantially constant along the length of the strut, and wherein the assembly is formed from graphite carbon-infiltrated carbon nanotubes (CI-CNTs).

11. The assembly of claim 10, wherein each strut includes an upper face and a lower, opposing face, and wherein each of the upper face and the lower face include a tapering profile through at least half a length of the strut.

12. The assembly of claim 10, wherein each strut includes an upper face and a lower, opposing face, and wherein only one of the upper face and the lower face includes a tapering profile through at least half a length of the strut.

13. The assembly of claim 10, wherein the tapering profile is a curvilinear profile.

14. The assembly of claim 10, wherein the tapering profile is a sloped line.

15. The assembly of claim 10, wherein the tapering profile is convex.

16. The assembly of claim 10, wherein the tapering profile is concave.

17. The assembly of claim 10, wherein the series of struts and end radii comprise a contiguous unit.

\* \* \* \* \*